United States Patent [19]

Sakuma et al.

[11] Patent Number: 5,290,172
[45] Date of Patent: Mar. 1, 1994

[54] METHOD FOR PREPARING A TOOTH SURFACE FOR BONDING

[75] Inventors: Tetsuro Sakuma, Tokorozawa; Yohji Imai, Chiba, both of Japan

[73] Assignee: GC Corporation, Tokyo, Japan

[21] Appl. No.: 937,399

[22] Filed: Aug. 31, 1992

[30] Foreign Application Priority Data

Nov. 6, 1991 [JP] Japan .................. 3-317379

[51] Int. Cl.$^5$ .............................. A61C 5/00
[52] U.S. Cl. .................. 433/215; 433/228.1; 106/35
[58] Field of Search .............. 433/215, 216, 228.1, 433/9, 24; 106/35

[56] References Cited

U.S. PATENT DOCUMENTS 4,588,756  5/1986  Bowen .............................. 433/228.1
5,023,107  6/1991  Roberts ............................ 433/228.1

FOREIGN PATENT DOCUMENTS 0310372  4/1989  European Pat. Off. .
0480785  4/1992  European Pat. Off. .

*Primary Examiner*—John J. Wilson
*Attorney, Agent, or Firm*—Oblon, Spivak, McClelland, Maier & Neustadt

[57] ABSTRACT

A method for treating a tooth surface to make it bondable well enough for dental purposes involves treating enamel and dentin with a primer comprising a) an organic acid, b) an iron, copper or cobalt salt and c) water, and then curing the tooth surface with a bonding material comprising d) a methacrylate or acrylate having at least one unsaturated double bond, e) a (thio)barbituric acid derivative and f) a polymerization initiator.

7 Claims, No Drawings

METHOD FOR PREPARING A TOOTH SURFACE FOR BONDING

BACKGROUND OF THE INVENTION

This invention relates generally to treating the surfaces of the teeth to make them adhesive to acrylic resin and, more specifically, to treating the surfaces of the teeth for restoring them and bonding dental composite material (composite resin) to them.

With a conventional adhesive for bonding restorative composite resin to enamel, a bonding strength higher than 100 kg/cm$^2$ that meets clinical requirements well enough is obtained between enamel and the restorative composite resin. This is true even when enamel is treated by acid etching using phosphoric or citric acid, then washed with water and dried, and finally coated with a bonding material which is composed of a methacrylic ester monomer and a curing agent and shows no adhesion to dentin. However, as only poor adhesion to dentin is obtained by using such bonding material having no adhesion to dentin, benzoyl peroxide/an aromatic tertiary amine/sulfinic acid initiators, etc. have been proposed in the art, as set forth Japanese Patent Publication Nos. 56-33363 and Japanese Patent Publication No. 15468. Still, no sufficient bond strength to dentin is obtained at all.

Various dentin treatment solutions or primers which have been said to have adhesion have been proposed. For instance, Japanese Patent Publication No. 55-30768 describes phosphoric ester compounds as being adhesive to dentin, but it fails to give the aforesaid high bonding strength, as measured by the present inventors. Japanese Patent Laid-Open No. 54-12338 discloses a functional monomer 4-methacryloxyethy trimellitic anhydride (hereinafter 4-META for short), and "Journal of the Japan Society for Dental Apparatus and Materials", 23(61), pp. 29-32 (1982) teaches that when dentin is treated with an aqueous solution of 10% citric acid and 3% ferric chloride and then restored with a restorative filler (4-META-containing methyl methacrylate/tri-n-butylborane/polymethyl methacrylate), a bonding strength of 12-18 MPa is obtained. When measured by the present inventors, however, such a high bonding strength could not be obtained.

On the other hand, it has turned out that (thio)barbituric acid derivative/copper compound/chlorine ion-based initiators are considerably effective in terms of bond strength to dentin. In this regard, see "the Journal of the Japan Research Society of Dental Materials and Appliances", Vol. 8, Special Issue No. 14, pp. 89-90 (1989).

However, they have quite the same problem as tri-n-butylborane in terms of the pre-treatment of a tooth surface; that is, they are troublesome to handle and, in addition, does not give sufficient bond strength. Thus, there is left much to be improved.

In view of the present state of the art where no clinically efficacious bonding material is obtained as yet, as already mentioned, we have investigated how to improve adhesion to dentin and, as a result, have accomplished the present invention.

SUMMARY OF THE INVENTION

In an effort to solve the state-of-the-art problem mentioned above, we have now discovered how to treat a tooth surface to make it bondable well enough based on a quite novel concept.

That is, the present invention provides a method for treating a tooth surface to make it bondable well enough for dental purposes, involving treating enamel and dentin with a primer comprising a) an organic acid, b) an iron, copper or cobalt salt and c) water, and then curing the tooth surface with a bonding material comprising d) a methacrylate or acrylate having at least one unsaturated double bond, e) a (thio)barbituric acid derivative and f) a polymerization initiator.

The iron, copper or cobalt salt in the primer and the barbituric acid derivative in the bonding material are provided with the mechanism of chemical polymerization initiation. It is believed that this enables the curing reaction of the monomer to occur from the surface of the tooth to be bonded, contributing to improving the adhesion to dentin. While the primer of this invention bears some resemblance to those set forth in Japanese Patent Laid-Open No. 61-183203, 62-231652, 64-90108 and 1-279815, they do not possibly involve such a curing mechanism as discovered by us. To add to this, the present invention is different from them in terms of what is intended. It is a matter of course that the bond strength measured by us with such primers is much lower than that achieved by the invention. The present invention lends itself suitable for recently developed, simple bonding systems as well.

DETAILED DESCRIPTION OF THE INVENTION

For the organic acid a), for instance, citric acid, succinic acid, oxalic acid, fumaric acid, tartaric acid, malic acid, maleic acid, ethylenediaminetetraacetic acid, polyacrylic acid and an acrylic acid/maleic acid copolymer may all be used. Preferably, the organic acid should be used at a concentration of 1-50% relative to the total weight of the primer.

For the iron, copper or cobalt salt b), use is made of ferric chloride, ferrous chloride, cupric chloride, cuprous chloride, copper sulfate, copper acetate and acetylacetone copper. Preferably, they should be used at a concentration of 0.0005 to 50% relative to the total weight of the primer.

For the methacrylate or acrylate d) which has at least one unsaturated double bond, use may be specifically made of methyl methacrylate, ethyl methacrylate, isopropyl methacrylate, 2-hydroxyethyl methacrylate, n-butyl methacrylate, isobutyl methacrylate, 3-hydroxypropyl methacrylate, tetrahydrofulfuryl methacrylate, glycidyl methacrylate, 2-methoxyethyl methacrylate, 2-ethylhyexyl methacrylate, benzil methacrylate 2,2-bis(methacryloxyphenyl)propane, 2,2-bis[4-(2-hydroxy-3-methacryloxypropoxy)phenyl]propane, 2,2-bis(4-methacryloxydiethoxyphenyl)propane, 2,2-bis(4-methacryloxypropoxyphenyl)propane, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate and pentaerythritol tetramethacrylate and their acrylates as well as methacrylates and acrylates containing an urethane bond in their molecules.

Note that particular preference is given to di-2-methacryloxyethyl-2,2,4-trimethylhexamethylene dicarbamate or its acrylate as well as a compound having the following structural formula:

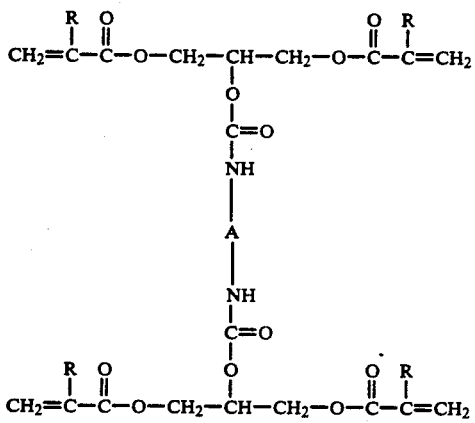

wherein:
R stands for an identical or different H or CH₃, and
—(A)— denotes —(CH₂)₆—,

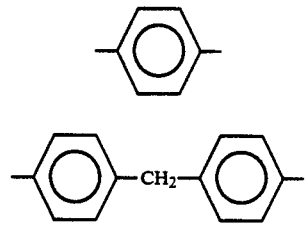

These methacrylates and acrylates are known as dental materials and may be used alone or in admixture at need.

For the (thio)barbituric acid derivative (e), by way of example alone, use may be made of 1,3,5-trimethyl(thio)barbituric acid, 1,3,5-triethyl(thio)barbituric acid, 1,3-dimethyl-5-ethyl(thio)barbituric acid, 1,5-dimethyl(thio)barbituric acid, 1-methyl-5-ethyl(thio)barbituric acid, 1-methyl-5-propyl(thio)barbituric acid, 5-ethyl(thio)barbituric acid, 5-propyl(thio)barbituric acid, 5-butyl(thio)barbituric acid, 1-benzyl-5-phenyl(thio)barbituric acid and 1-cyclohexyl-5-ethyl(thio)barbituric acid. These derivatives should preferably be used at a concentration of 0.1 to 10% with respect to the total weight of the dental bonding material. More preferably and in view of a curing reaction with the iron, copper or cobalt salt, use is made of 1-cyclohexyl-5-ethyl(thio)barbituric acid which gives a colorless cured product.

In recent years, photopolymerization initiators have often been used as the polymerization initiator f), and for them sensitizer-reducer combinations are now generally used. The sensitizers used, for instance, may include camphor quinone, benzyl, diacetyl, benzyl dimethyl ketal, benzyl diethyl ketal, benzyl di(2-methoxyethyl)ketal, 4,4'-dimethylbenzyl-dimethyl ketal, anthraquinone, 1-chloroanthraquinone, 2-chloroanthraquinone, 1,2-benzanthraquinone, 1-hydroxyanthraquionone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthioxanthone, thioxanthone-10, 10-dioxide, thioxanthone-10-oxide, benzoin methyl ether, benzoin ethyl ether, isopropyl ether, benzoin isobytyl ether, benzophenone, bis-(4-dimethylaminophenyl) ketone, 4,4'-bisdiethylaminobenzophenone and azide group-containing-compounds, which may be used alone or in combination of two or more.

In general, tertiary amines may be used as the reducing agent. The tertiary amines used, for instance, may preferably include dimethylaminoethyl methacrylate, triethanolamine, 4-dimethylaminomethyl benzoate, 4-dimethylaminoethyl benzoate and 4-dimethylaminoisoamyl benzoate. Other reducing agents, for instance, benzoyl peroxide, sulfinic acid derivatives and organometal compounds, may be used as well.

The thus obtained photopolymerization type of adhesive compositions are polymerized by exposure to active rays such as ultraviolet or visible rays. The light sources used to this end, for instance, may include various forms of ultrahigh, high, intermediate and low pressure mercury lamps, chemical lamps, carbon arc lamps, metal halide lamps, fluorescent lamps, tungsten lamps, xenon lamps and argon ion lasers.

As the chemical polymerization initiator, use may be made of benzoyl peroxide-tertiary amine, benzoyl peroxide-N-phenylglycine, benzoyl peroxide-sodium p-toluenesulfinate, benzoyl peroxide-sodium benzenesulfinate, benzoyl peroxide-sodium p-toluenesulfinate or sodium benzenesulfinate-aromatic tertiary amine, potassium persulfate-aromatic tertiary amine and sodium persulfate-aromatic tertiary amine.

As occasion arises, slight amounts of UV absorbers, coloring agents, polymerization inhibitors, etc. may be used optionally with fillers, solvents and so on. The tooth surface primer and adhesive material may generally be provided in one- or two-pack, powder/liquid, one- or two-paste forms. In addition, they may be made available in the form of a photopolymerization type glass ionomer containing (meth)acrylates, which is now commercially available.

EXAMPLES

This invention will now be explained more specifically but not exclusively with reference to the following examples.

A primer was prepared, consisting of citric acid (10 parts by weight), ferric chloride (3 parts by weight) and distilled water (87 parts by weight). Then, an adhesive material was prepared, consisting of 2-hydroxyethyl methacrylate (70 parts by weight), 2,2-bis[4-(2-hydroxy-3-methacryloxy-propoxy)phenyl]propane (30 parts by weight), 1-cyclohexyl-5-ethylbarbituric acid (1.0 part by weight), camphor quinone (0.5 parts by weight) and dimethylaminoethyl methacrylate (1.0 part by weight).

With the primer and bonding material mentioned above, bond strength and fitness tests were carried out as follows. The compositions and amounts used as well as the test results are set out in Table 1.

HOW TO MEASURE BONDING STRENGTH

1. The surfaces of fresh bovin anteriorteeth were polished by a #600 water-resistant abrasive paper with the addition of water until the dentinal and enamel surfaces, five each, were exposed to view.

2. The polished surfaces were coated with the primer mentioned above for 40 seconds, followed by water washing and drying.

3. Each dentinal surface was coated with the photopolymerization type bonding material through a cellophane tape having 3.0 mm diameter pores applied onto it, which was in turn thinly spread with the use of air and exposed to the light from a GC's dental irradiator ("GC Light") for 20 seconds. The chemical polymerization type of two-pack bonding system was kneaded together, coated and thinly spread with air.

4. A GC's photopolymerization type composite resin ("Graft LC") was built up on an adhesion surface with a 2.0 mm thick silicone rubber mold having a pore of 5.0 mm in internal diameter, and exposed to light from a GC light for 40 seconds for curing.

5. After immersed in water of 37° C. for one day, a test piece with a tensile acrylic rod mounted on it was pulled at a crosshead speed of 1.0 mm/min on a Shimazu autograph for tensile adhesion testing. For estimation of the bond strengths to enamel and dentin, five measurements each were averaged.

HOW TO OBSERVE IN WHAT RESIN COMPOSITION WAS FIT

1. A saucer type cavity was formed in the axial face of a human extracted true molar.

2. According to the strength measuring procedures above, a dental adhesive composition was coated on the tooth, and a photopolymerization type composite resin was filled in the cavity for curing. Note that the enamel was etched with phosphoric acid in conventional manners.

3. After cured, the test piece was held in water of 37° C. for 24 hours. After that, the central region of the cavity was horizontally cut perpendicularly with respect to the axis, and the section was smoothened with No. 1000 emery paper while water was poured thereon.

4. After the section was slightly corroded with a phosphoric acid solution, a precision replica of that section was formed. In what state the resin was bonded to the dentinal surface was observed by observing the replica surface under an SEM.

5. Fitness assay was made according to Sasazaki's method for measuring resin/dentin gaps (cf. the "Japanese Journal of Conservative Dentistry", Vol. 28, No. 2, pp. 452–478 (1985)). The assay was made according to five ranks a, b, c, d and e, v.s. a: no gap found, indicating that excellent fitness is achieved.

a: fitness excellent, no gap.
b: a slight gap.
c: a gap of 5 $\mu$m or less.
d: a gap of 5–10 $\mu$m.
e: a gap of 10 $\mu$m or more.

EXAMPLES 2~13

With the primers and bonding materials shown in Tables 1~3, the same tests as referred to in Example 1 were done.

TABLE 1

| | Primer | | Bonding Material (Photopolymerization Type) | | Bond Strength (kg/cm²) Enamel | Dentin | Fitness |
|---|---|---|---|---|---|---|---|
| Example 1 | Citric acid | 10.0 p/b/w | 2-hydroxyethylmethacrylate | 70.0 p/b/w | 151 | 126 | a |
| | Ferric chloride | 3.0 | 2,2-bis[4-(2-hydroxy-3-methacryloxypropoxy)phenyl]propane | 30.0 | | | |
| | Distilled water | 87.0 | 1-cyclohexyl-5-ethylbarbituric acid | 1.0 | | | |
| | | | Camphor quinone | 0.5 | | | |
| | | | Dimethylaminoethylmethacrylate | 1.0 | | | |
| Example 2 | Polyacrylic acid | 10.0 p/b/w | 2-hydroxyethylmethacrylate | 70.0 p/b/w | 138 | 115 | a |
| | Ferric chloride | 3.0 | 2,2-bis[4-(2-hydroxy-3-methacryloxypropoxy)phenyl]propane | 30.0 | | | |
| | Distilled water | 87.0 | 1-cyclohexyl-5-ethylbarbituric acid | 1.0 | | | |
| | | | Camphor quinone | 0.5 | | | |
| | | | Dimethylaminoethylmethacrylate | 1.0 | | | |
| Example 3 | Citric acid | 10.0 p/b/w | 2,2-bis(4-methacryloxypolyethoxyphenyl)propane | 100.0 p/b/w | 154 | 135 | a |
| | Cupric chloride | 3.0 | 1-cyclohexyl-5-ethylbarbituric acid | 1.0 | | | |
| | Distilled water | 87.0 | Camphor quinone | 0.5 | | | |
| | | | Dimethylaminoethylmethacrylate | 1.0 | | | |
| Example 4 | Oxalic acid | 3.0 p/b/w | 2,2-bis(4-methacryloxypolyethoxyphenyl)propane | 100.0 p/b/w | 178 | 127 | a |
| | Acetylacetone copper | 1.0 | 1-cyclohexyl-5-ethylbarbituric acid | 1.0 | | | |
| | Distilled water | 96.0 | Camphor quinone | 0.5 | | | |
| | | | Dimethylaminoethylmethacrylate | 1.0 | | | |
| Example 5 | Ethylenediamine tetraacetic acid | 17.0 p/b/w | Triethyleneglycoldimethacrylate | 50.0 p/b/w | 152 | 132 | a |
| | Ferric chloride | 3.0 | 2,2-bis[4-(2-hydroxy-3-methacryloxypropoxy)phenyl]propane | 50.0 | | | |
| | Distilled water | 80.0 | 1-cyclohexyl-5-ethylbarbituric acid | 1.0 | | | |
| | | | Camphor quinone | 0.5 | | | |
| | | | Dimethylaminoethylmethacrylate | 1.0 | | | |

*p/b/w = parts by weight

TABLE 2

| | Primer | | Bonding Material (Photopolymerization Type) | | Bond Strength (kg/cm²) Enamel | Dentin | Fitness |
|---|---|---|---|---|---|---|---|
| Example 6 | Citric acid | 10.0 p/b/w | 2-hydroxyethylmethacrylate | 70.0 p/b/w | 131 | 116 | a |
| | Ferric chloride | 0.1 | 2,2-bis[4-(2-hydroxy-3-methacryloxypropoxy)phenyl]propane | 30.0 | | | |
| | Distilled water | 90.0 | 1-cyclohexyl-5-ethylbarbituric acid | 1.0 | | | |
| | | | Camphor quinone | 0.5 | | | |

TABLE 2-continued

| | Primer | | Bonding Material (Photopolymerization Type) | | Bond Strength (kg/cm²) Enamel | Dentin | Fitness |
|---|---|---|---|---|---|---|---|
| Example 7 | Polyacrylic acid | 50.0 p/b/w | Dimethylaminoethylmethacrylate | 1.0 | 108 | 131 | a |
| | Ferric chloride | 3.0 | 2-hydroxyethylmethacrylate | 70.0 p/b/w | | | |
| | Distilled water | 47.0 | 2,2-bis[4-(2-hydroxy-3-methacryloxypropoxy)phenyl]propane | 30.0 | | | |
| | | | 1-cyclohexyl-5-ethylbarbituric acid | 5.0 | | | |
| | | | Camphor quinone | 0.5 | | | |
| | | | Dimethylaminoethylmethacrylate | 1.0 | | | |
| Example 8 | Citric acid | 5.0 p/b/w | 2,2-bis(4-methacryloxypolyethoxyphenyl)propane | 100.0 p/b/w | 100 | 105 | a |
| | Cupric chloride | 0.001 | | | | | |
| | Distilled water | 95.0 | 1-cyclohexyl-5-ethylbarbituric acid | 8.0 | | | |
| | | | Camphor qunione | 0.5 | | | |
| | | | Dimethylaminoethylmethacrylate | 1.0 | | | |
| Example 9 | Oxalic acid | 1.0 p/b/w | 2,2-bis(4-methacryloxypolyethoxyphenyl)propane | 100.0 p/b/w | 117 | 129 | a |
| | Acetylacetone copper | 1.0 | | | | | |
| | Distilled water | 96.0 | 1-cyclohexyl-5-ethylbarbituric acid | 1.0 | | | |
| | | | Camphor quinone | 0.5 | | | |
| | | | Dimethylaminoethylmethacrylate | 1.0 | | | |
| Example 10 | Ethylenediamine tetraacetic acid | 17.0 p/b/w | Triethyleneglycoldimethacrylate | 50.0 p/b/w | 135 | 112 | a |
| | Ferric chloride | 20.0 | 2,2-bis[4-(2-hydroxy-3-methacryloxypropoxy)phenyl]propane | 50.0 | | | |
| | Distilled water | 63.0 | 1-cyclohexyl-5-ethylbarbituric acid | 0.1 | | | |
| | | | Camphor quinone | 0.5 | | | |
| | | | Dimethylaminoethylmethacrylate | 1.0 | | | |

*p/b/w = parts by weight

TABLE 3

| | Primer | | Bonding Material (Photopolymerization Type) | | Bond Strength (kg/cm²) Enamel | Dentin | Fitness |
|---|---|---|---|---|---|---|---|
| Example 11 | Citric acid | 10.0 p/b/w | (Liquid A) | | 165 | 111 | a |
| | Cupric chloride | 3.0 | 2-hydroxyethylmethacrylate | 70.0 p/b/w | | | |
| | Distilled water | 87.0 | 2,2-bis[4-(2-hydroxy-3-methacryloxypropoxy)phenyl]propane | 30.0 | | | |
| | | | 1-cyclohexyl-5-ethylbarbituric acid | 1.0 | | | |
| | | | N,N-dihydroxyethylparatoluidine | 1.0 | | | |
| | | | (Liquid B) | | | | |
| | | | 2-hydroxyethylmethacrylate | 70.0 p/b/w | | | |
| | | | 2,2-bis[4-(2-hydroxy-3-methacryloxypropoxy)phenyl]propane | 30.0 | | | |
| | | | Benzoyl peroxide | 1.0 | | | |
| Example 12 | Copolymer of acrylic acid/maleic acid | 10.0 p/b/w | (Liquid A) | | 149 | 123 | a |
| | Ferric chloride | 3.0 | Ethanol | 100.0 p/b/w | | | |
| | Distilled water | 87.0 | N,N-dihydroxyethylparatoluidine | 1.0 | | | |
| | | | P-toluenesulfinate soda | 1.0 | | | |
| | | | 1-cyclohexyl-5-ethylbarbituric acid | 1.0 | | | |
| | | | (Liquid B) | | | | |
| | | | 2-hydroxyethylmethacrylate | 70.0 p/b/w | | | |
| | | | 2,2-bis[4-(2-hydroxy-3-methacryloxypropoxy)phenyl]propane | 30.0 | | | |
| | | | Benzoyl peroxide | 1.0 | | | |
| Example 13 | Citric acid | 10.0 p/b/w | (Liquid A) | | 168 | 140 | a |
| | Acetylacetone copper | 3.0 | Ethanol | 100.0 p/b/w | | | |
| | Distilled water | 87.0 | 1-cyclohexyl-5-ethylbarbituric acid | 1.0 | | | |
| | | | N-phenylglycine | 1.0 | | | |
| | | | (Liquid B) | | | | |
| | | | 2-hydroxyethylmethacrylate | 100.0 p/b/w | | | |
| | | | Benzoyl peroxide | 1.0 | | | |

*p/b/w = parts by weight

COMPARATIVE EXAMPLES 1~10

For the purpose of comparison, the same tests as referred to in Example 1 were done, using the primers and bonding materials shown in Tables 4~6, which do not contain the components a), b) and e) essentially required in this invention or depart from the quantitative ranges defined by this invention.

TABLE 4

| | Primer | | Bonding Material (Photopolymerization Type) | | Bond Strength (kg/cm²) Enamel | Dentin | Fitness |
|---|---|---|---|---|---|---|---|
| Comparative Example 1 | Citric acid | 10.0 p/b/w | (Photopolymerization Type) | | 145 | 30 | c |
| | Ferric chloride | 3.0 | 2-hydroxyethylmethacrylate | 70.0 p/b/w | | | |

TABLE 4-continued

| | Primer | | Bonding Material (Photopolymerization Type) | | Bond Strength (kg/cm²) Enamel | Dentin | Fitness |
|---|---|---|---|---|---|---|---|
| | Distilled water | 87.0 | 2,2-bis[4-(2-hydroxy-3-methacryloxypropoxy)phenyl]propane | 30.0 | | | |
| | | | Camphor quinone | 0.5 | | | |
| Comparative | Citric acid | 10.0 p/b/w | Dimethylaminoethylmethacrylate | 1.0 | | | |
| Example 2 | Ferric chloride | 3.0 | (Chemical Polymerization Type) | | 144 | 18 | d |
| | Distilled water | 87.0 | (Liquid A) | | | | |
| | | | Ethanol | 100.0 p/b/w | | | |
| | | | N,N-dihydroxyethylparatoluidine | 1.0 | | | |
| | | | P-toluenesulfinate soda | 1.0 | | | |
| | | | (Liquid B) | | | | |
| | | | 2-hydroxyethylmethacrylate | 70.0 p/b/w | | | |
| | | | 2,2-bis[4-(2-hydroxy-3-methacryloxypropoxy)phenyl]propane | 30.0 p/b/w | | | |
| Comparative | Polyacrylic acid | 10.0 p/b/w | Benzoyl peroxide | 1.0 | | | |
| Example 3 | Cupric chloride | 3.0 | (Photopolymerization Type) | | 110 | 24 | d |
| | Distilled water | 87.0 | 2,2-bis(4-methacryloxypolyethoxyphenyl)propane | 100.0 p/b/w | | | |
| | | | Camphor quinone | 0.5 | | | |
| Comparative | Citric acid | 10.0 p/b/w | Dimethylaminoethylmethacrylate | 1.0 | | | |
| Example 4 | Distilled water | 90.0 | (Photopolymerization Type) | | 137 | 35 | d |
| | | | 2,2-bis(4-methacryloxypolyethoxyphenyl)propane | 100.0 p/b/w | | | |
| | | | 1-cyclohexyl-5-ethylbarbituric acid | 1.0 | | | |
| | | | Camphor quinone | 0.5 | | | |
| | | | Dimethylaminoethylmethacrylate | 1.0 | | | |

*p/b/w = parts by weight

TABLE 5

| | Primer | | Bonding Material (Photopolymerization Type) | | Bond Strength (kg/cm²) Enamel | Dentin | Fitness |
|---|---|---|---|---|---|---|---|
| Comparative | Ferric chloride | 3.0 p/b/w | 2-hydroxyethylmethacrylate | 70.0 p/b/w | 10 | 19 | d |
| Example 5 | Distilled water | 97.0 | 2,2-bis[4-(2-hydroxy-3-methacryloxypropoxy)phenyl]propane | 30.0 | | | |
| | | | 1-cyclohexyl-5-ethylbarbituric acid | 1.0 | | | |
| | | | Camphor quinone | 0.5 | | | |
| | | | Dimethylaminoethylmethacrylate | 1.0 | | | |
| Comparative | Polyacrylic acid | 0.5 p/b/w | 2-hydroxyethylmethacrylate | 70.0 p/b/w | 9 | 25 | d |
| Example 6 | Ferric chloride | 3.0 | 2,2-bis[4-(2-hydroxy-3-methacryloxypropoxy)phenyl]propane | 30.0 | | | |
| | Distilled water | 96.5 | 1-cyclohexyl-5-ethylbarbituric acid | 1.0 | | | |
| | | | Camphor quinone | 0.5 | | | |
| | | | Dimethylaminoethylmethacrylate | 1.0 | | | |
| Comparative | Maleic acid | 55.0 p/b/w | 2,2-bis(4-methacryloxypolyethoxyphenyl)propane | 100.0 p/b/w | 123 | 24 | c |
| Example 7 | Cupric chloride | 3.0 | 1-cyclohexyl-5-ethylbarbituric acid | 1.0 | | | |
| | Distilled water | 42.0 | Camphor quinone | 0.5 | | | |
| | | | Dimethylaminoethylmethacrylate | 1.0 | | | |
| Comparative | Oxalic acid | 15.0 p/b/w | 2,2-bis(4-methacryloxypolyethoxyphenyl)propane | 100.0 p/b/w | 155 | 18 | c |
| Example 8 | Copper chloride | 55.0 | 1-cyclohexyl-5-ethylbarbituric acid | 1.0 | | | |
| | Distilled water | 30.0 | Camphor quinone | 0.5 | | | |
| | | | Dimethylaminoethylmethacrylate | 1.0 | | | |
| Comparative | Ethylenediaminetetraacetic acid | 17.0 p/b/w | Triethyleneglycoldimethacrylate | 50.0 p/b/w | 161 | 21 | d |
| Example 9 | Ferric chloride | 3.0 | 2,2-bis[4-(2-hydroxy-3-methacryloxypropoxy)phenyl]propane | 50.0 | | | |
| | Distilled water | 80.0 | 1-cyclohexyl-5-ethylbarbituric acid | 0.05 | | | |
| | | | Camphor quinone | 0.5 | | | |
| | | | Dimethylaminoethylmethacrylate | 1.0 | | | |

*p/b/w = parts by weight

TABLE 6

| | Primer | | Bonding Material (Photopolymerization Type) | | Bond Strength (kg/cm²) Enamel | Dentin | Fitness |
|---|---|---|---|---|---|---|---|
| Comparative | Citric Acid | 10.0 p/b/w | (Liquid A) | | 53 | 11 | d |
| Example 10 | Cupric chloride | 3.0 | 2-hydroxyethylmethacrylate | 40.0 p/b/w | | | |
| | Distilled water | 87.0 | 2,2-bis[4-(2-hydroxy-3-methacryloxypropoxy)phenyl]propane | 35.0 | | | |
| | | | 1-cyclohexyl-5-ethylbarbituric acid | 25.0 | | | |
| | | | N,N-dihydroxyethylparatoluidine | 1.0 | | | |

TABLE 6-continued

| Primer | Bonding Material (Photopolymerization Type) | Bond Strength (kg/cm$^2$) | | |
|---|---|---|---|---|
| | | Enamel | Dentin | Fitness |
| | (Liquid B) | | | |
| | 2-hydroxyethylmethacrylate | 70.0 p/b/w | | |
| | 2,2-bis[4-(2-hydroxy-3-methacryloxypropoxy) phenyl]propane | 30.0 | | |
| | Benzoyl peroxide | 1.0 | | |

*p/b/w = parts by weight

The method of this invention has been found to give particularly strong bond strength to dentin. It has also turned out that in the human removed teeth observed, the resin is well bonded to the dentin and there is not any gap between them, which is said to be a leading cause of secondary caries.

What is claimed is:

1. A method for treating a tooth surface to make it bondable well enough for dental purposes, involving treating enamel and dentin with a primer comprising a) an organic acid, b) an iron, copper or cobalt salt and c) water, and then curing the tooth surface with a bonding material comprising d) a methacrylate or acrylate having at least one unsaturated double bond, e) a (thio)barbituric acid derivative and f) a polymerization initiator.

2. A method as claimed in claim 1, wherein said organic acid is at least one acid selected from the group consisting of citric acid, oxalic acid, maleic acid, ethylenediamine-tetraacetic acid, polyacrylic acid and an acrylic acid/maleic acid copolymer.

3. A method as claimed in claim 1 or 2, wherein the concentration of said organic acid lies in the range of 1 to 50% based on the total weight of said primer.

4. A method as claimed in any one of claims 1 or 2, wherein said iron, copper or cobalt salt is ferric chloride, cupric chloride or acetylacetone copper.

5. A method as claimed in any one of claims 1 or 2, wherein the concentration of said iron, copper or cobalt salt lies in the range of 0.0005 to 50% based on the total weight of said primer.

6. A method as claimed in any one of claims 1 or 2, wherein said (thio)barbituric acid derivative is 1-cyclohexyl-5-ethylbarbituric acid.

7. A method as claimed in any one of claims 1 or 2, wherein the concentration of said (thio)barbituric acid derivative lies in the range of 0.1 to 10% based on the total weight of said bonding material.

* * * * *